(12) United States Patent
Bierhoff et al.

(10) Patent No.: US 9,775,587 B2
(45) Date of Patent: Oct. 3, 2017

(54) SPIRAL BIOPSY DEVICE

(71) Applicant: KONINKLIJKE PHILIPS N.V., Eindhoven (NL)

(72) Inventors: Waltherus Cornelis Jozef Bierhoff, Veldhoven (NL); Franciscus Marinus Antonius Maria Van Gaal, Heeze (NL); Bernardus Hendrikus Wilhelmus Hendriks, Eindhoven (NL); Vishnu Vardhan Pully, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 139 days.

(21) Appl. No.: 14/440,706

(22) PCT Filed: Nov. 22, 2013

(86) PCT No.: PCT/IB2013/060323
§ 371 (c)(1),
(2) Date: May 5, 2015

(87) PCT Pub. No.: WO2014/080366
PCT Pub. Date: May 30, 2014

(65) Prior Publication Data
US 2015/0297198 A1    Oct. 22, 2015

Related U.S. Application Data

(60) Provisional application No. 61/729,665, filed on Nov. 26, 2012.

(51) Int. Cl.
*A61B 10/02* (2006.01)
*A61B 10/04* (2006.01)
(Continued)

(52) U.S. Cl.
CPC ........ *A61B 10/0266* (2013.01); *A61B 5/0066* (2013.01); *A61B 5/0075* (2013.01);
(Continued)

(58) Field of Classification Search
CPC ... A61B 5/0066; A61B 5/0075; A61B 5/0086; A61B 5/742
See application file for complete search history.

(56) References Cited

U.S. PATENT DOCUMENTS 2,623,552 A * 12/1952 Compton ............... B27G 13/02
144/240
4,955,882 A   9/1990 Hakky
(Continued)

FOREIGN PATENT DOCUMENTS

EP      2022405 A1     2/2009
RU      2217057 C1     11/2003
WO   WO 2012068315 A1 * 5/2012 ......... A61B 10/0266

OTHER PUBLICATIONS

Nachabe, R. et al., "Estimation of lipid and water concentrations in scattering media with diffuse optical spectroscopy from 900 to 1600 nm", J. Biomed. Opt. 15, 037015 (2010).
(Continued)

*Primary Examiner* — Long V Le
*Assistant Examiner* — Yi-Shan Yang

(57) ABSTRACT

A biopsy device is proposed comprising a shaft and a tubular member. The shaft is movably, i.e. rotatably as well as shiftably accommodated within the tubular member and comprises a spiral at a distal end portion of the shaft, wherein the spiral is formed by a twisted sheet. Such a spiral may be considered as a laterally open thread having no solid core.

16 Claims, 7 Drawing Sheets

(51) Int. Cl.
*A61B 5/00* (2006.01)
*A61B 5/1459* (2006.01)

(52) U.S. Cl.
CPC .......... *A61B 5/0086* (2013.01); *A61B 5/1459* (2013.01); *A61B 5/6857* (2013.01); *A61B 5/742* (2013.01); *A61B 10/04* (2013.01); *A61B 5/0071* (2013.01)

(56) References Cited

U.S. PATENT DOCUMENTS

| | | | |
|---|---|---|---|
| 5,488,958 A | 2/1996 | Topel et al. | |
| 6,083,237 A | 7/2000 | Huitema et al. | |
| 6,174,291 B1 * | 1/2001 | McMahon | A61B 5/0071 600/564 |
| 7,008,381 B2 | 3/2006 | Janssens | |
| 8,317,727 B2 | 11/2012 | Peliks | |
| 8,920,450 B2 | 12/2014 | Zeroni et al. | |
| 2006/0142779 A1 * | 6/2006 | Arramon | A61B 17/3421 606/92 |
| 2008/0249553 A1 * | 10/2008 | Gruber | A61B 17/32002 606/171 |
| 2008/0306405 A1 | 12/2008 | Masseglia et al. | |
| 2010/0198149 A1 | 8/2010 | Fox | |
| 2012/0197157 A1 | 8/2012 | Ryan et al. | |
| 2013/0046316 A1 | 2/2013 | Sullivan et al. | |
| 2013/0197551 A1 * | 8/2013 | Yoon | A61B 17/32002 606/170 |

OTHER PUBLICATIONS

Farrell, T.J. et al., "A diffusion theory model of spatially resolved, steady-state diffuse reflectance for the non-invasive determination of tissue optical properties", Med. Phys. 19 (1992) p. 879-888.

Nachabe, R. et al., "Estimation of biological chromophores using diffuse optical spectroscopy: benefit of extending the UV-VIS wavelength range to include 1000 to 1600 nm", Optics Express, vol. 18, 2010, pp. 1432-1442.

Zhang, Q. et al., "Turbidity-free fluorescence spectroscopy of biological tissue", Opt. Lett 25 (2000) p. 1451.

* cited by examiner

SPIRAL BIOPSY DEVICE

CROSS-REFERNCE TO PRIOR APPLICATIONS

This application is the U.S. National Phase application under 35U.S.C. §371 of International Application Serial No. PCT/IB2013/060323, filed on Nov. 22, 2013, which claims the benefit of U.S. Application Ser. No. 61/729,665, filed on Nov. 26, 2012. These applications are hereby incorporated by reference herein.

FIELD OF THE INVENTION

The invention generally relates to a biopsy device including a spiral for taking a tissue sample. Particularly, the invention relates to a biopsy device with integrated optical fibers, for tissue inspection based on diffuse reflectance and autofluorescence measurements to diagnose whether tissue is cancerous or not, before extracting tissue.

BACKGROUND OF THE INVENTION

Various biopsy devices exist in order to take a tissue sample of a suspicious lesion in the body. Most of these devices consist of pushing forward an inner part containing a notch followed by pushing forward an outer cylindrical knife to cut out the tissue bulged in the notch of the inner part. Although useful in several situations, in cases near critical structures or when small samples need to be taken this is a less preferred solution.

Another way of taking biopsies is by using a biopsy forceps. In order to employ the forceps an open space is required for instance taking a biopsy of a wall in a hollow organ such as the bladder, lung etc. In solid tissue however this concept cannot be used. Furthermore, by using a forceps the sample is torn off the tissue rather than well controlled cutting.

Another example of a biopsy device is a Spirotome biopsy device. It is based on turning a cutting helix into the lesion, followed by a cutting cannula. The helix is formed on a solid inner core in the form of a screw-thread on this inner core. As a result a relative small tissue sample can be taken compared to the total volume that is covered by the device.

SUMMARY OF THE INVENTION

The problem is thus how to design a medical device that is capable of taking a biopsy in a controlled way, avoiding side effects, being applicable in small sized biopsy needles. This and further objects are solved by the subject-matter of the independent claim. Further embodiments are described in the dependent claims.

Generally, a biopsy device comprises a shaft and a tubular member. The shaft is movably, i.e. rotatably as well as shiftably accommodated within the tubular member and comprises a spiral at a distal end portion of the shaft, wherein the spiral is formed by a twisted sheet. Such a spiral may be considered as a laterally open thread having no solid core.

The spiral may comprise a sharpened distal edge for securely cutting tissue in front of the spiral.

According to an embodiment, the biopsy device further comprises a cutting edge arranged at outer edges of adjacent windings of a thread of the spiral. Such a cutting edge may be formed by a blade which is arranged laterally at the outer edges of windings of the twisted sheet. The edge may be substantially parallel to a longitudinal axis of the spiral, but may also be slanted relative to that axis. Preferably, the cutting edge is inclined with an acute angle in the range of 10 degree to 25 degree, According to a further embodiment, the tubular member of the biopsy device may include a sharpened distal front surface. With such a tubular member, tissue enclosed within the thread of the twisted sheet can be cut laterally and along the thread.

According to another embodiment, the device is capable of providing tissue feedback of the location where the biopsy is going to be taken. Therefore, the biopsy device may further comprise at least one optical fiber arranged in the tubular member, with a distal front surface of the optical fiber located at a distal end of the tubular member.

The biopsy device may further comprise a cutting tube with a sharpened distal edge, wherein the cutting tube is accommodated within the tubular member and wherein the shaft is accommodated within the cutting tube. Such a cutting tube may improve the possibility to withdraw the tissue sample out of the tubular member, in a case in which it is intended to let the tubular member, i.e. the outermost part of the device, remain at a biopsy location, for example, for taking more than one biopsy. Furthermore, it may be possible, to accommodate at least one optical fiber in the tubular member so that the sharpened edge of the cutting tube would be separated from the optical fiber and a tissue inspection by means of the optical fiber might be performed independently from the extraction of a tissue sample.

According to an embodiment, the twisted sheet may form a double thread so that the spiral comprises two windings at each cross section along a longitudinal direction of the spiral.

The biopsy device may be formed as a straight and stiff needle. Alternatively, the biopsy device may be formed as a flexible catheter. Thus, the biopsy device may comprise a flexible shaft at the distal end of which the spiral may be arranged so that the flexible shaft can drive the rotational and translational movements of the spiral. Further, the biopsy device may comprise a flexible tube at the end of which the tubular member, especially the distal cutting edge as described above may be arranged. Additionally, the biopsy device may comprise a further flexible tube for supporting the cutting tube so that cutting of tissue by means of the cutting tube may be actuated remotely by means of that flexible tube.

According to another embodiment, the biopsy device further comprises a console including a light source, a light detector and a processing unit for processing the signals provided by the light detector, wherein one of the light source and the light detector may provide wavelength selectivity. The light source may be one of a laser, a light-emitting diode or a filtered light source, and the console may further comprise one of a fiber switch, a beam splitter or a dichroic beam combiner. Furthermore, the device may be adapted to perform at least one out of the group consisting of diffuse reflectance spectroscopy, diffuse optical tomography, differential path length spectroscopy, and Raman spectroscopy.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted that similar elements are provided with the same reference signs in different figures, if appropriate.

DETAILED DESCRIPTION OF EMBODIMENTS

Figure 1:
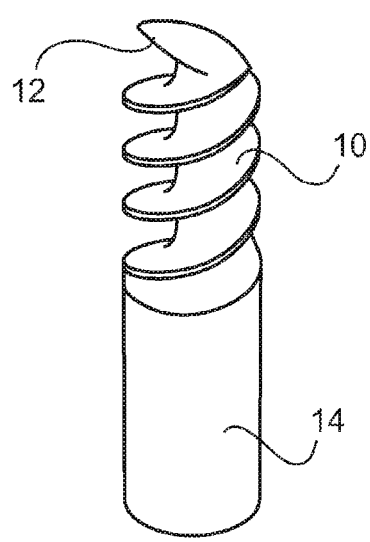
FIG. 1 is an illustration of a shaft of a biopsy device.

FIG. 1 shows a first embodiment of a shaft, in particular a distal end portion of a shaft of a biopsy device wherein a spiral 10 is formed at a distal end portion of the shaft 14. The spiral 10 is formed by a twisted helical sheet so that a double thread is formed. The double helical structure comprises a first and a second sharpened front surface 12 at a distal end of the spiral. By means of the sharpened front surface 12, the spiral is capable of cutting into tissue in a helical way, when the spiral is driven into tissue by rotation and shifting, simultaneously. It is noted that the rotational and translational movements may be synchronized, i.e. adjusted relative to each other so that the spiral may penetrate even soft tissue like a thread of a screw would typically penetrate hard tissue, i.e. substantially without displacing any surrounding tissue.

Figure 2:
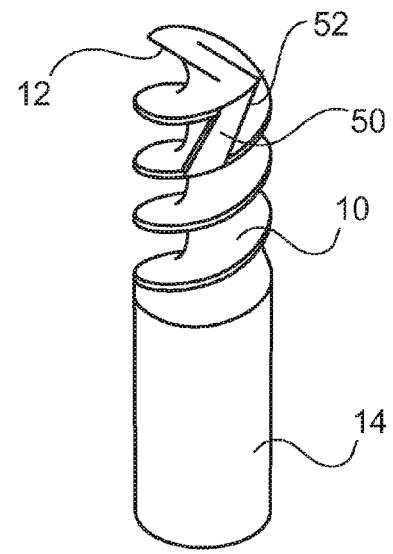
FIG. 2 is an illustration of a shaft of a biopsy device.

FIG. 2 shows a second embodiment of a shaft of a biopsy device, the shaft comprising a twisted helical sheet 10, like the spiral according to the first embodiment. Furthermore, the shaft comprises a knife or blade 50 with a cutting edge 52. The blade is laterally attached to outer edges of two adjacent windings of the spiral thread. In this embodiment, the cutting edge 52 commences at one of the radially outer edges of the sharpened distal front surface 12 of the helical sheet and extends proximally with a small angle relative to the longitudinal axis of the spiral, wherein the distal end of the cutting edge 52 is located in a circumferential direction, i.e. a rotational direction slightly before the proximal end of the cutting edge 52, i.e. with an offset. The blade 50 has a dimension in a circumferential direction which is smaller than a dimension in a longitudinal direction.

It may be appreciated that more than one blade 50 is provided at the spiral 10, for example, there may be a second blade opposite to the blade 50 shown in FIG. 2, with the second blade commencing at the opposite radially outer edge of the sharpened front surface 12. It will be understood that the blade 50 may also have a larger dimension in a circumferential direction than in a longitudinal direction.

The space within the spiral 10 may hold a specimen in a fixed position whereas the blade 50 may cut the specimen free from the surrounding tissue while the spiral penetrates into tissue.

Figure 3:
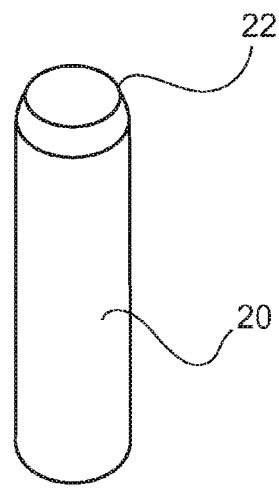
FIG. 3 is an illustration of a tubular member of a biopsy device.

FIG. 3 shows an embodiment of a tubular member 20 of a biopsy device. The tubular member 20 is a hollow member, i.e. comprises a through bore in a longitudinal direction, and comprises a sharpened distal edge 22 for cutting tissue along the outer side of the shaft. The through bore is adapted to accommodate a shaft, for example a shaft as shown in FIG. 1 or in FIG. 2.

Figure 4:
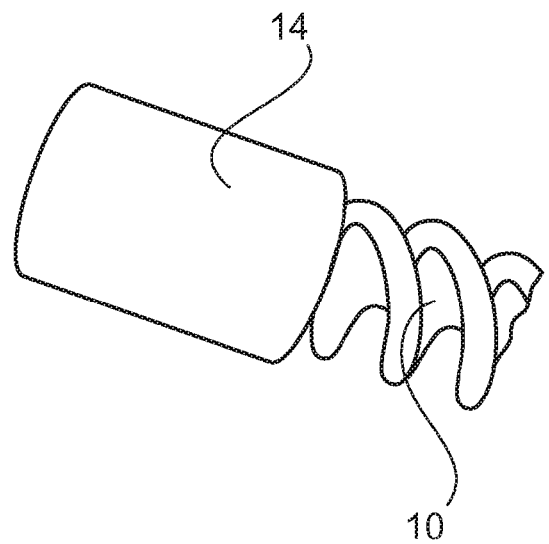
FIG. 4 is an isometric view of a shaft with a spiral.
Figure 5:
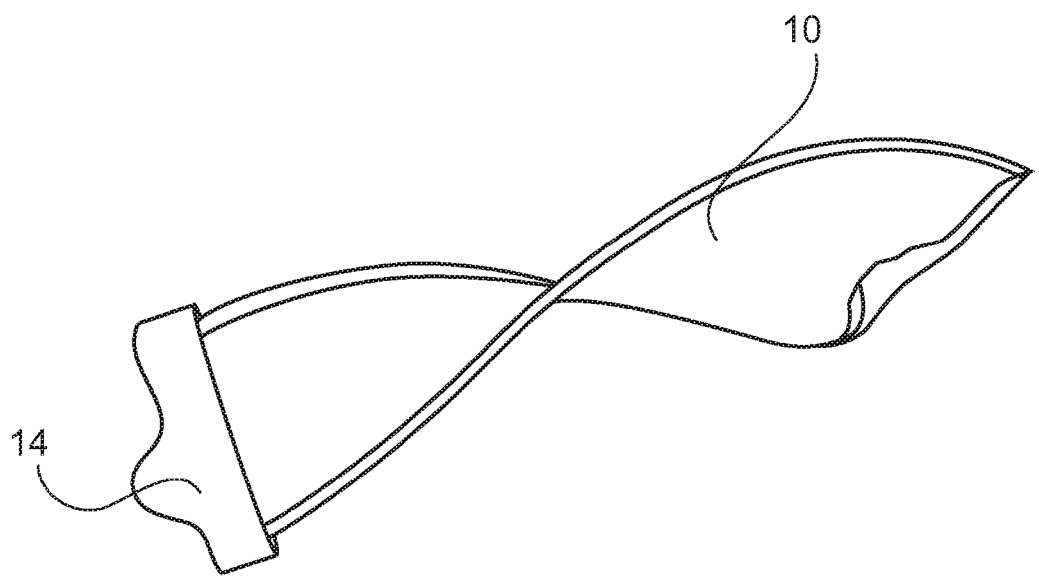
FIG. 5 is an isometric view of a shaft with another spiral.

FIGS. 4 and 5 are isometric illustrations of a third and a fourth embodiment of a shaft with proximal a shaft portion 14 and a distal spiral 10, wherein the spirals 10 differ with respect of the pitch of the twisted helix.

Figure 6:
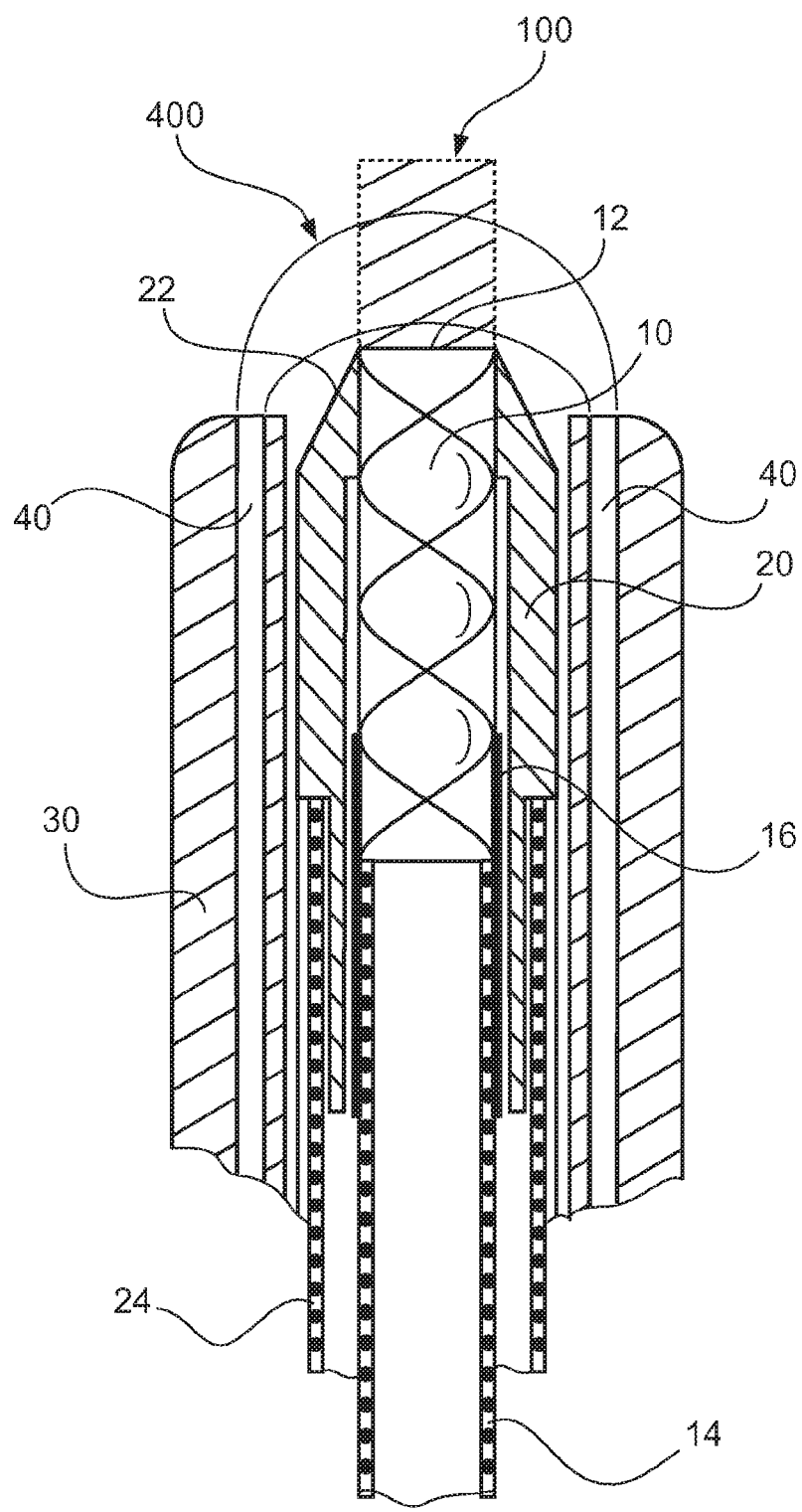
FIG. 6 is a sectional view of a biopsy device.

FIG. 6 shows a biopsy device according to an embodiment, comprising an inner shaft, an intermediate as well as an outer tubular member. The shaft is formed by a proximal portion 14 which may be bendable so that this proximal portion 14 may serve as a flexible driving portion, and a distal end portion 10 which comprises a spiral as described for example with reference to FIG. 1. The proximal portion 14 and the distal portion 10 are coupled by means of an element 16. The intermediate tubular member is formed as a cutting tube having a rigid distal end portion 20 with a sharpened distal edge 22, and a proximal portion 24 which may be bendable as the portion 14 of the shaft. The distal end portion 20 includes a section with a reduced outer diameter so that the proximal portion 24 may be attached so as to overlap the distal end portion 20 and forming a press fit. The proximal portion 24 may be adapted to drive the distal end portion 20 so as to cut tissue along the spiral 10 of the shaft.

In an embodiment in which the inner shaft and the outer cutting tube are actuated via flexible cables or tubes, only the tip, i.e. the part by which a biopsy may actually be taken, needs to be rigid, while the rest remains flexible. In this way the biopsy device is compatible with catheter-like or endoscope-like biopsy devices.

The outer tubular member 30 may include channels for accommodating optical fibers 40. As shown in FIG. 6, the optical fibers 40 may be arranged so that an optical tissue inspection may be performed in an area 400 schematically depict directly in front of the distal tip of the biopsy device. Also schematically depict is an area 100 in which tissue may be extracted by means of the spiral 10 when the shaft with the spiral is moved forwardly into the tissue.

The optical fibers may be arranged within the tubular member 30 with the distal ends of the optical fibers at the side and at the front of the cutting part. At least one fiber may be located at one side of the cutting tool and the other fiber is located at the opposite side of the cutting tool such that when emitting light at one end of the fiber and collecting the light with the other fiber the light has travelled and thus interrogated the tissue that is to be biopted. The optical fibers may be connected to a console capable of sending and receiving light (see FIG. 8). The console is capable of spectrally resolving the received light and able to perform diffuse optical spectroscopy, fluorescence spectroscopy, RAMAN spectroscopy, optical coherence tomography (OCT), differential path length spectroscopy.

Figure 7:
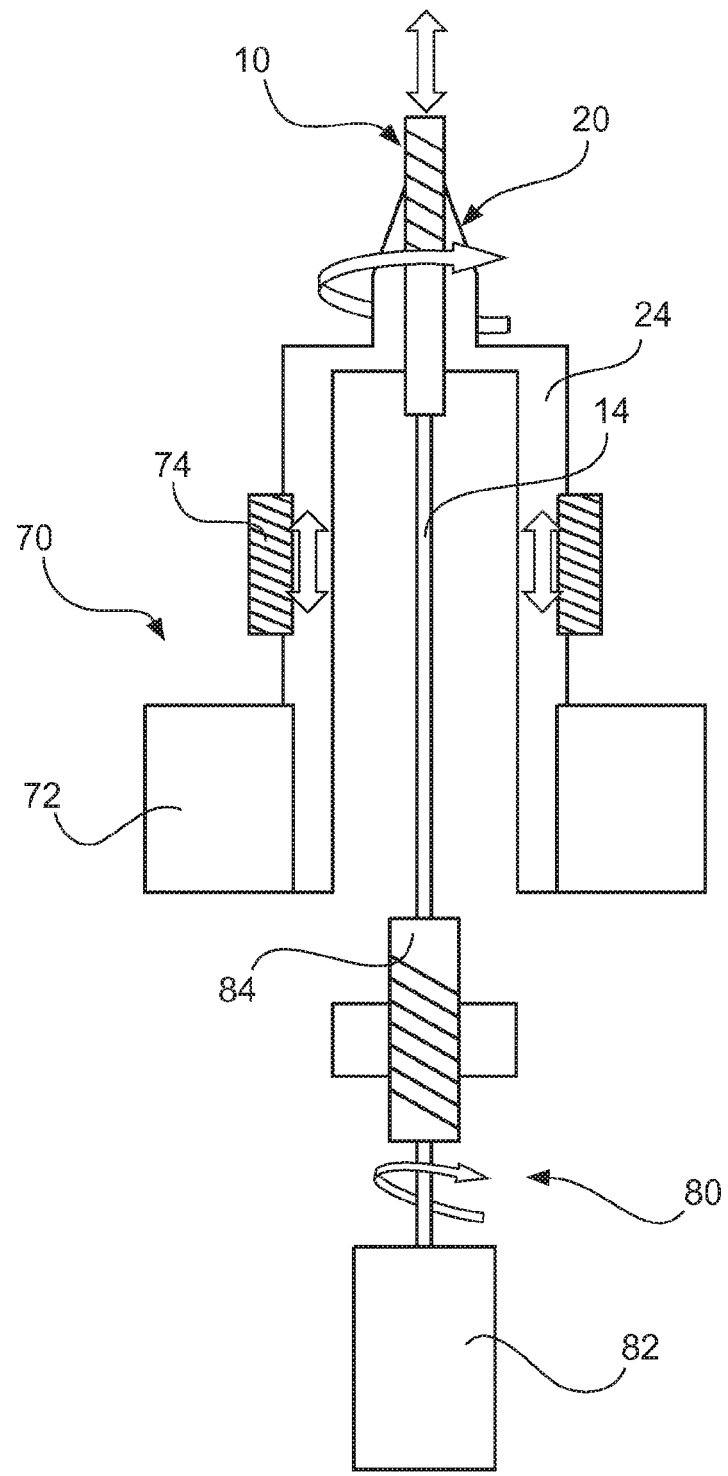
FIG. 7 is a schematically illustration of movements of parts of the biopsy device relative to each other.

FIG. 7 illustrates mechanical actuation of the parts of the biopsy device. The proximal portion 14 of the shaft may be driven by a first actuation unit 80 whereas the cutting tube may be driven by a second actuation unit 70.

The spiral 10, i.e. the twisted helical knife is driven by a flexible hollow driving shaft 14. Shaft 14 may be made hollow to allow vacuum assist biopsy. The specimen can be sucked away through the hollow driving shaft after it is released from the surrounding tissue. The first actuation unit 80 comprises a first motor 82 and a first nut 84 for driving the shaft of the twisted helical knife. The first nut 84 forces the pitch of the forward movement. The nut pitch should be equal to the pitch of the spiral 10. In this way the spiral only cuts itself into the tissue without destroying or displacing the tissue.

The second actuation unit 70 comprises a second motor 72 and a second nut 74 for driving the outside cutting tube 20. To achieve best cutting properties the tube may rotate during the movement forward. This is realized by rotating the shaft 24 with second motor 72 and the second nut 74 to force the shaft forward in a controlled way. It is noted that the driving shaft of first actuation unit 80 may extend through the shaft of the second actuation unit 70. The rotation and translation of the two shafts 14 and 24 can also be realized with motors with rotation and translation capability.

The whole biopsy taking sequence can be automated. The physician only has to activate the steering electronics to start taking the biopsy, for example by pushing a button on the handset of a catheter, wherein the whole driving mechanism can be located inside the handset of the catheter. Furthermore, the handset with driving mechanism can be made reusable by making the handset detachable from the catheter tubing.

A computer program for controlling the biopsy taking sequence, executable on the processor may be provided on a suitable medium such as an optical storage medium or a solid-state medium supplied together with or as part of the processor, but may also be distributed in other forms, such as via the Internet or other wired or wireless telecommunication systems.

Figure 8:
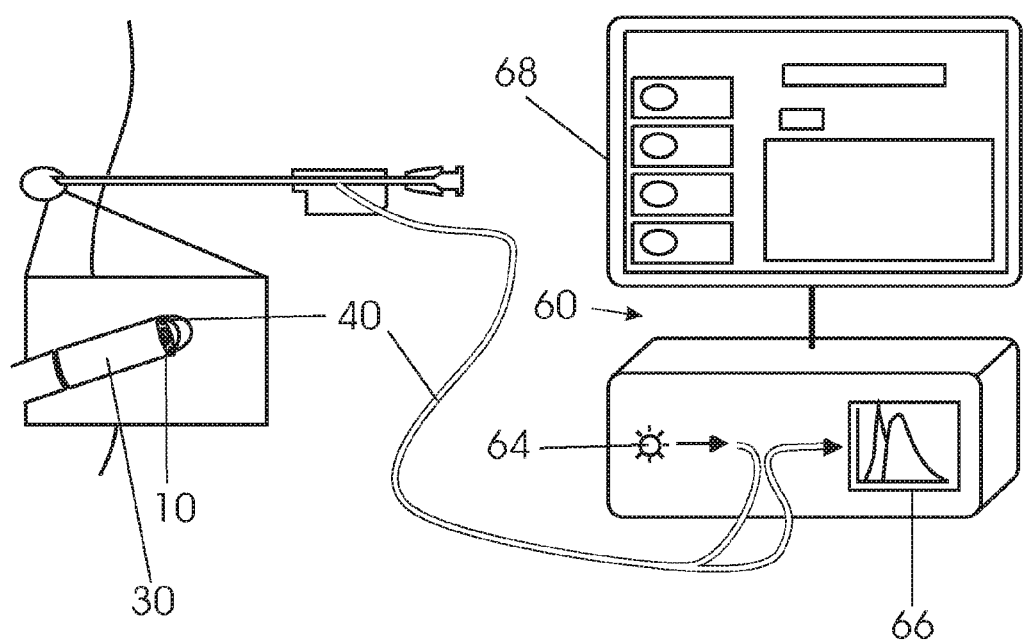
FIG. 8 shows a system including a needle and a console.

As shown in FIG. 8, the fibers 40 of the biopsy device are connected to an optical console 60. The optical fibers can be understood as light guides or optical waveguides. In an embodiment, the console 60 comprises a light source 64 in the form of a halogen broadband light source with an embedded shutter, and an optical detector 66. The optical detector 66 can resolve light with a wavelength substantially in the visible and infrared regions of the wavelength spectrum, such as from 400 nm to 1700 nm. The combination of light source 64 and detector 66 allows for diffuse reflectance measurements. For a detailed discussion on diffuse reflectance measurements see R. Nachabé, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

On the other hand, also other optical methods can be envisioned like diffuse optical tomography by employing a plurality of optical fibers, differential path length spectroscopy, fluorescence spectroscopy, optical coherence tomography and Raman spectroscopy to extract tissue properties.

A processor, i.e. a computer software executed by the processor transforms the measured spectrum into physiological parameters that are indicative for the tissue state and a monitor 68 may be used to visualize the results.

For fluorescence measurements the console must be capable of providing excitation light to at least one source fiber while detecting tissue-generated fluorescence through one or more detection fibers. The excitation light source may be a laser (e.g. a semiconductor laser), a light-emitting diode (LED) or a filtered light source, such as a filtered mercury lamp. In general, the wavelengths emitted by the excitation light source are shorter than the range of wavelengths of the fluorescence that is to be detected. It is preferable to filter out the excitation light using a detection filter in order to avoid possible overload of the detector by the excitation light. A wavelength-selective detector, e.g. a spectrometer, is required when multiple fluorescent entities are present that need to be distinguished from each other.

In case fluorescence measurements are to be combined with diffuse reflectance measurements, the excitation light for measuring fluorescence may be provided to the same source fiber as the light for diffuse reflectance. This may be accomplished by, e.g., using a fiber switch, or a beam splitter or dichroic beam combiner with focusing optics. Alternatively, separate fibers may be used for providing fluorescence excitation light and light for diffuse reflectance measurements.

To perform spectroscopy, the acquired spectra may be fitted using a custom made Matlab 7.9.0 (Mathworks, Natick, Mass.) algorithm. In this algorithm, a widely accepted analytical model was implemented, namely the model introduced by the reference T. J. Farrel, M. S. Patterson and B. C. Wilson, "A diffusion theory model of spatially resolved, steady-state diffuse reflectance for the non-invasive determination of tissue optical properties", Med. Phys. 19 (1992) p. 879-888, which is hereby incorporated by reference in entirety. The input arguments for the model of this reference are the absorption coefficient $\mu_a(\lambda)$, the reduced scattering coefficient $\mu'_s(\lambda)$ and the center-to-center distance between the emitting and collecting fibers at the tip of the probe.

In the following part, the model will be explained briefly. The used formulas are mainly based on work of Nachabé et al., and reference is thus made to R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442, which is hereby incorporated by reference in entirety, and furthermore reference is made to R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010), which is also hereby incorporated by reference in entirety.

A double power law function can be used to describe the wavelength dependence of the reduced scattering, where the wavelength $\lambda$ is expressed in nm and is normalized to a wavelength value of $\lambda_0=800$ nm. The parameter a corresponds to the reduced scattering amplitude at this specific wavelength.

$$\mu_s(\lambda) = a\left(\rho_{MR}\left(\frac{\lambda}{\lambda_0}\right)^{-b} + (1-\rho_{MR})\left(\frac{\lambda}{\lambda_0}\right)^{-4}\right)[cm^{-1}] \quad \text{(Eq. 1)}$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted b and is related to the particle size. For a homogeneous distribution of absorbers, the total light absorption coefficient, $\mu_\alpha(\lambda)$ can be computed as products of the extinction coefficients and volume fraction of the absorbers (see FIG. 9)

$$\mu_\alpha^{Total} = f_1\mu_\alpha^1 + f_2\mu_\alpha^2 + f_3\mu_\alpha^3 + \quad \text{(Eq. 2)}$$

Instead of modeling the absorption coefficient $\mu_\alpha(\lambda)$ as the sum of absorption coefficients weighted by the respective concentrations of the four chromophores of interest, it was decided to express the tissue absorption coefficient as $$\mu_\alpha^{Tissue}(\lambda) = C(\lambda)\nu_{Blood}\mu_\alpha^{Blood}(\lambda) + \nu_{WL}\mu_\alpha^{WL}(\lambda)[cm^{-1}] \quad \text{(Eq. 3)}$$

where $\mu_\alpha^{Blood}(\lambda)$ corresponds to the absorption by blood and $\mu_\alpha^{WL}(\lambda)$ corresponds to absorption by water and lipid together in the probed volume. The volume fraction of water and lipid is $\nu_{WL}=[Lipid]+[H_2O]$, whereas $\nu_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as $$C(\lambda) = \frac{1 - \exp(-2R\mu_\alpha^{Blood}(\lambda))}{2R\mu_\alpha^{Blood}(\lambda)} \quad \text{(Eq. 4)}$$

where R denotes the average vessel radius expressed in cm. The absorption coefficient related to blood is given by $$\mu_\alpha^{Blood}(\lambda) + \alpha_{BL}\mu_\alpha^{HbO_2}(\lambda) + (1-\alpha_{BL})\mu_\alpha^{Hb}(\lambda)[cm^{-1}] \quad \text{(Eq. 5)}$$

where $\mu_\alpha^{HbO_2}(\lambda)$ and $\mu_\alpha^{Hb}(\lambda)$ represent the basic extinction coefficient spectra of oxygenated hemoglobin $HbO_2$ and deoxygenated hemoglobin Hb, respectively. The oxygenated hemoglobin fraction in the total amount of hemoglobin is noted $\alpha_{BL}=[HbO_2]/([HbO_2]+[Hb])$ and is commonly known as the blood oxygen saturation. The absorption due to the presence of water and lipid in the measured tissue is defined as $$\mu_\alpha^{WL}(\lambda) = \alpha_{WL}\mu_\alpha^{Lipid}(\lambda) + (1-\alpha_{WL})\mu_\alpha^{H_2O}(\lambda)[cm^{-1}] \quad \text{(Eq. 6)}$$

In this case the concentration of lipid related to the total concentration of lipid and water together can be written as $\alpha_{WF}=[Lipid]/([Lipid]+[H_2O])$, where [Lipid] and [$H_2O$] correspond to the concentration of lipid (density of 0.86 g/ml) and water, respectively.

This way of relating the water and lipid parameters in the expression of the absorption coefficient defined in Eq. 6, rather than estimating separately the water and lipid volume fraction corresponds to a minimization of the covariance of the basic functions for fitting resulting in a more stable fit cf. the reference R. Nachabe, B. H. W. Hendriks, M. van der Voort, A. E., and H. J. C. M. Sterenborg "Estimation of biological chromophores using diffuse optical spectroscopy: benefit of extending the UV-VIS wavelength range to include 1000 to 1600 nm", Optics Express, vol. 18, 2010, pp. 1432-1442. For further explanation and validation of this theorem reference is made to the reference R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

For example by means of the described algorithm optical tissue properties may be derived such as the scattering coefficient and absorption coefficient of different tissue chromophores: e.g. hemoglobin, oxygenated haemoglobin, water, fat etc. These properties are different between normal healthy tissue and diseased (cancerous) tissue.

Figure 9:
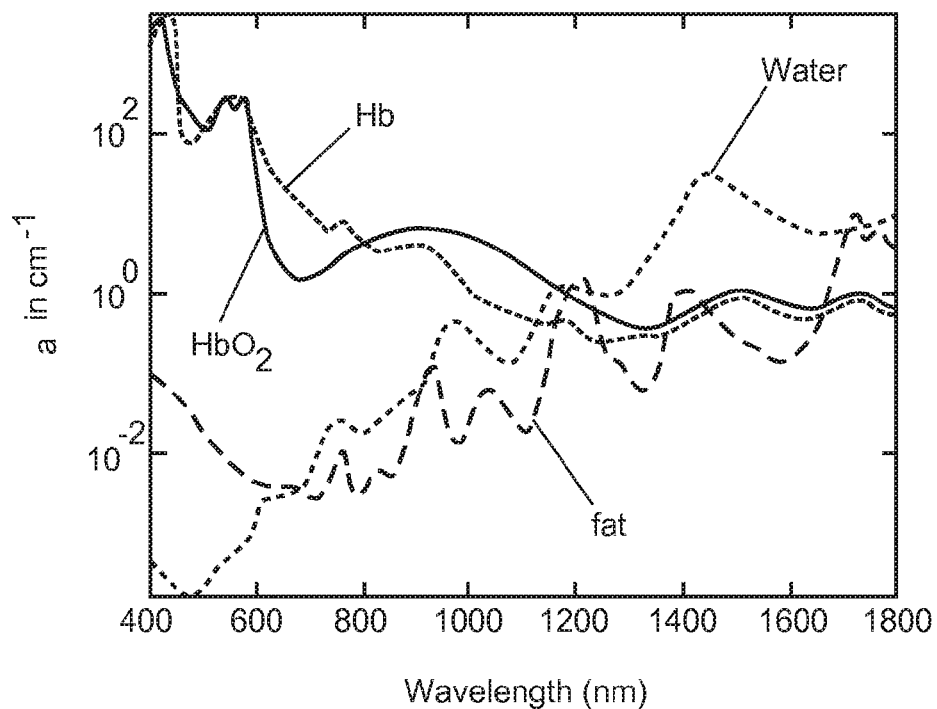
FIG. 9 shows a log plot of absorption coefficient of blood, water and fat.

The main absorbing constituents in normal tissue dominating the absorption in the visible and near-infrared range are blood (i.e. hemoglobin), water and fat. By fitting the model to the measurement while using the power law for scattering, the volume fractions of the blood, water and fat as well as the scattering coefficient may be determined. In FIG. 9 the absorption coefficient of these chromophores as a function of the wavelength are presented. It is noted that blood dominates the absorption in the visible range, while water and fat dominate in the near infrared range.

Figure 10:
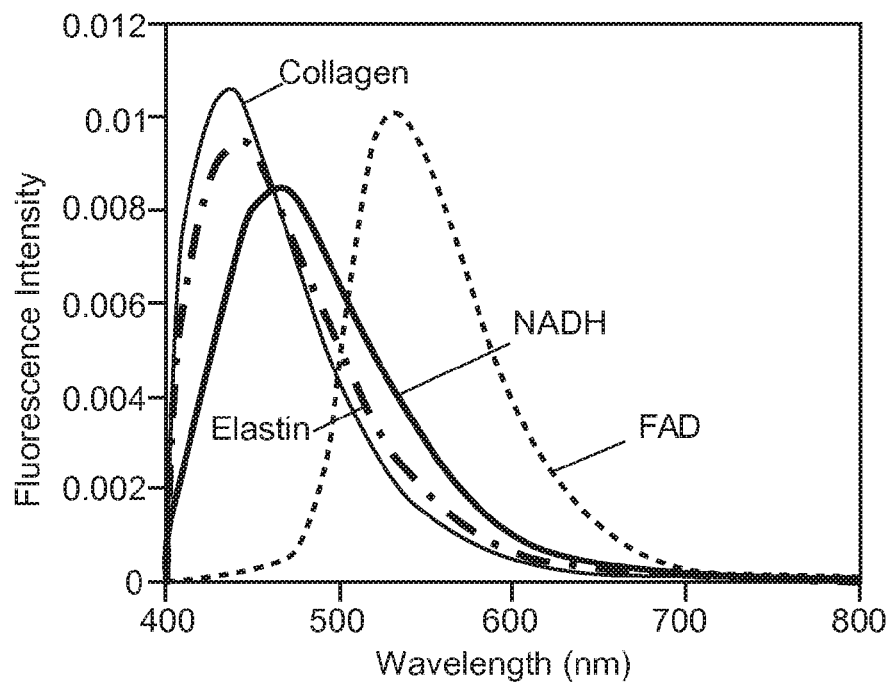
FIG. 10 shows fluorescence curves for collagen, elastin, NADH and FAD.

Apart from diffuse reflectance also fluorescence may be measured. For instance parameters like collagen, elastin, NADH and FAD could be measured (see FIG. 10). Especially, the ratio NADH/FAD, which is called the optical redox parameter, may be of interest because it is an indicator for the metabolic state of the tissue (see Ref. Q. Zhang, M. G. Mueller, J. Wu and M. S. Feld, "Turbidity-free fluorescence spectroscopy of biological tissue" Opt. Lett. 25 (2000) p 1451 and references therein), which is assumed to change upon effective treatment of cancer cells.

The biopsy device may be used in minimally invasive needle interventions such as low-back pain interventions or taking biopsies in the field of cancer diagnosis or in case where tissue characterization around the needle is required.

In the following, exemplary needles will be described with respect to their outer diameter, their insertion length, and their preferred use.

A biopsy needle might have an outer diameter of 1.27 mm up to 2.108 mm, might be inserted into tissue with 100 mm to 150 mm of its length, and might be used in soft tissue core biopsies in the neck, the head, the breast, the prostate, and the liver.

A fine aspiration needle of soft tissue might have an outer diameter between 0.711 mm and 2.108 mm, might be inserted into soft tissue with 100 mm to 150 mm of its length, and might be used for aspiration of soft tissue.

A brain biopsy needle might have an outer diameter of 2.108 mm, might be inserted into tissue with 150 mm up to 250 mm of its length, and might be used for diagnostic brain biopsies.

Finally, the device may include a needle electrode having an outer diameter of 2.108 mm and smaller, the electrode might be inserted into tissue up to 250 mm of its length, and might be used for radiofrequency ablation for instance of tumors.

Figure 11:
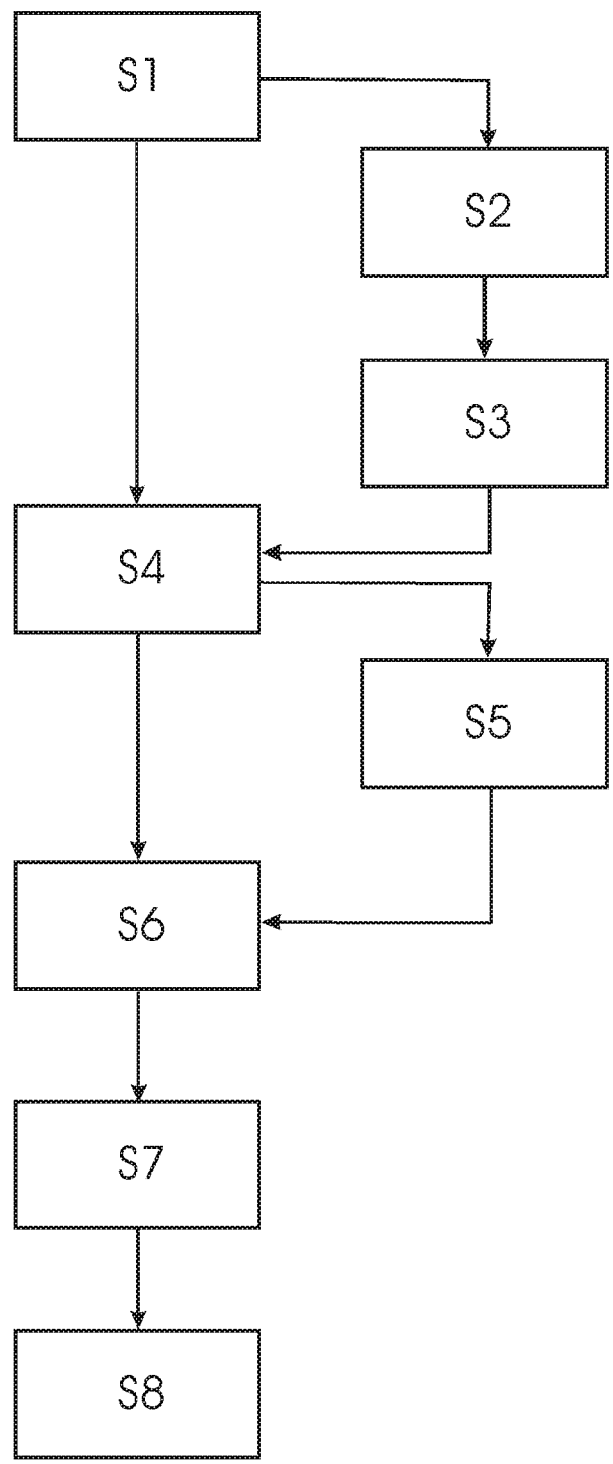
FIG. 11 is a flow chart illustrating steps of operating a biopsy device.

The flow-chart in FIG. 11 illustrates the principle of the steps performed in accordance with an embodiment described herein. It will be understood that the steps described, are major steps, wherein these major steps might be differentiated or divided into several sub-steps. Furthermore, there might be also sub-steps between these major steps.

In step S1, the biopsy device may be positioned at a desired location in a tissue. This may be performed under image guidance.

In step S2, for example in a case in which an outer tubular member is provided which includes optical fibers, an optical measurement of the tissue in front of the tip of the optical biopsy device may be performed.

In step S3, the tissue type may be determined. In case the result is not satisfying, the biopsy device may be repositioned.

In step S4, the inner shaft with the spiral is pushed forward while turning so that a helical cut is achieved. This step is performed both in a case in which no tissue inspection is needed or intended, for example when using an outer tubular member which does not include any optical fibers (directly following step S1) and in a case in which an outer tubular member is provided which includes optical fibers and an optical tissue inspection has been performed (following step S3).

It is noted that step S4 may include cutting of lateral tissue, in a case in which a blade is laterally attached to the windings of the spiral so as perform that lateral cutting simultaneously with the provision of a helical cut.

In step S5, in case the biopsy device is equipped with a cutting tube, this tube is pushed forward so as to cut the tissue along the inner shaft, i.e. the spiral, except for the distal front part. It is noted that this step is omitted when the biopsy device does not include such cutting tube.

In step S6, the shaft is rotated with at least one turn, without forward movement, to cut the biopsy at the front from the surrounding tissue.

In step S7, the biopsy device as a whole or firstly an inner part and secondly an outer part of the device is withdrawn, depending on the configuration of the biopsy device and the intended application.

Finally, the extracted specimen or tissue sample is taken out of the helical knife so as to be analysed.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 spiral of shaft
12 distal cutting front surface
14 proximal portion of shaft
16 coupling element
20 cutting tube
22 distal cutting edge
24 proximal portion of cutting tube
30 outer tubular member/catheter
40 optical fiber
50 lateral blade
52 cutting edge
60 console
64 light source
66 light detector
68 monitor
70 second actuation unit
72 second motor
74 second nut
80 first actuation unit
82 first motor
84 first nut
100 area to take a biopsy
400 area of tissue inspection

The invention claimed is:

1. A biopsy device comprising
   a shaft, and
   a tubular member,
   wherein the shaft is movably accommodated within the tubular member,
   wherein the shaft comprises a continuous spiral at a distal end portion of the shaft,
      wherein the continuous spiral is formed by a twisted sheet, and
   wherein the biopsy device further comprises a blade with a cutting edge, the blade being laterally attached to outer edges of two adjacent windings of a thread of the continuous spiral, and the blade extending proximally with a small angle relative to the longitudial axis of the continuous spiral.

2. The biopsy device of claim 1, wherein the continuous spiral comprises a sharpened distal front surface.

3. The biopsy device of claim 1, wherein the tubular member is a cutting tube having a sharpened distal edge.

4. The biopsy device of claim 1, further comprising an outer tubular member, wherein the tubular member is accommodated within the outer tubular member, and wherein the tubular member is a cutting tube having a sharpened distal end.

5. The biopsy device of claim 1, further comprising an optical fiber arranged in the tubular member, with a distal front surface of the optical fiber located at a distal end of the tubular member.

6. The biopsy device of claim 1, wherein the twisted sheet forms a double thread so that the continuous spiral comprises two windings at each cross section along a longitudinal direction of the continuous spiral.

7. The biopsy device of claim 1, wherein the biopsy device is formed as a flexible catheter, such that at least a portion of each of the shaft and the tubular member is flexible, enabling bending of the at least a portion of each of the shaft and the tubular member.

8. The biopsy device of claim 1, further comprising a console including a light source, a light detector and a processing unit for processing the signals provided by the light detector.

9. The biopsy device of claim 8, wherein one of the light source and light detector provides wavelength selectivity.

10. The biopsy device of claim 8, wherein the light source is one of a laser, a light-emitting diode or a filtered light source.

11. The biopsy device of claim 8, wherein the console further comprises one of a fiber switch, a beam splitter or a dichroic beam combiner.

12. The biopsy device of claim 8, being adapted to perform at least one out of the group consisting of diffuse reflectance spectroscopy, diffuse optical tomography, differential path length spectroscopy, optical coherence tomography and Raman spectroscopy.

13. The biopsy device of claim 8, wherein the console further comprises a monitor.

14. A biopsy device comprising:
   an outer tubular member;
   an intermediate tubular member located within the outer tubular member, such that a distal end of the intermediate tubular member extends past a distal end of the outer tubular member,
      wherein the intermediate tubular member comprises a sharped distal edge at the distal end of the intermediate tubular member; and a shaft located within the intermediate tubular member, the shaft being movable such that a distal end of the shaft is extendable past the distal end of the intermediate tubular member and rotatable within the intermediate tubular member, wherein the distal end of the shaft comprises a continuous spiral formed by a twisted sheet and the continuous spiral comprises a sharpened distal front surface for taking a sample of tissue, and
a bade with a cutting edge, wherein the blade being laterally attached to outer edges of two adjacent windings of a thread of the continuous spiral, and the blade extending proximally with a small angle relative to the longitudinal axis of the continuous spiral.

15. The biopsy device of claim 14, wherein the sharped distal edge at the distal end of the intermediate tubular member cuts sampled tissue enclosed within a thread of the twisted sheet, laterally and along the thread.

16. The biopsy device of claim 14, wherein the outer tubular member defines at least one channel for accommodating at least one optical fiber, with a front surface of the at least one optical fiber located at the distal end of the tubular member, enabling optical inspection of tissue in front of the distal end of the outer tubular member, including the tissue to be sampled.

* * * * *